(12) United States Patent
Park et al.

(10) Patent No.: US 8,017,390 B2
(45) Date of Patent: Sep. 13, 2011

(54) METHOD FOR THE PREPARATION OF DERMAL PAPILLA TISSUE EMPLOYING MESENCHYMAL STEM CELLS

(75) Inventors: Jung-Keug Park, Seoul (KR); Hee-Hoon Yoon, Incheon (KR); Bo-Young Yoo, Seoul (KR); Young-Jin Kim, Seoul (KR); Youn-Ho Shin, Daejeon (KR)

(73) Assignee: Dongguk University Industry-Academic Cooperation Foundation, Seoul (KR)

( * ) Notice: Subject to any disclaimer, the term of this patent is extended or adjusted under 35 U.S.C. 154(b) by 411 days.

(21) Appl. No.: 12/282,760

(22) PCT Filed: Jul. 20, 2007

(86) PCT No.: PCT/KR2007/003514
§ 371 (c)(1),
(2), (4) Date: Sep. 12, 2008

(87) PCT Pub. No.: WO2009/014272
PCT Pub. Date: Jan. 29, 2009

(65) Prior Publication Data
US 2010/0261276 A1 Oct. 14, 2010

(51) Int. Cl.
*C12N 5/077* (2010.01)
*C12N 5/02* (2006.01)

(52) U.S. Cl. ........ 435/325; 435/377; 435/404; 435/405; 435/406; 435/372; 435/384

(58) Field of Classification Search .................. None
See application file for complete search history.

(56) References Cited

U.S. PATENT DOCUMENTS

| | | |
|---|---|---|
| 6,497,875 B1 | 12/2002 | Sorrell et al. |
| 6,887,490 B1 | 5/2005 | Jahoda et al. |
| 6,991,813 B2 | 1/2006 | Xu |
| 2007/0258956 A1 | 11/2007 | Higgins |
| 2007/0298017 A1 | 12/2007 | Han |
| 2008/0145929 A1 | 6/2008 | Park |

FOREIGN PATENT DOCUMENTS

WO 2007/089798 A2 8/2007

OTHER PUBLICATIONS

Inamatsu et al., Journal of Investigative Dermatology (1998) Nov;111(5):767-775.*
Hoogduijn, M.J. et al., "Comparative Characterization of Hair Follicle Dermal Stem Cells and Bone Marrow Mescenchymal Stem Cells," Stems Cells and Development, 15, pp. 49-60, 2006.
Kataoka, K., et al., "Participation of Adult Mouse Bone Marrow Cells in Reconstitution of Skin," Am. J. of Pathology, 163:4, Oct. 2003, 1227-31.

* cited by examiner

*Primary Examiner* — Daniel C Gamett
(74) *Attorney, Agent, or Firm* — Sughrue Mion, PLLC (57) ABSTRACT

A method for the preparation of dermal papilla tissue comprising the step of culturing mesenchymal stem cells in a medium having a specific composition is provided. The method makes it possible to form in vitro a quantity of dermal papilla tissues having hair follicle inducting ability and, accordingly, it can be effectively used for the treatment of alopecia through cell transplantation.

8 Claims, 7 Drawing Sheets

METHOD FOR THE PREPARATION OF DERMAL PAPILLA TISSUE EMPLOYING MESENCHYMAL STEM CELLS

This is a national stage application under 35 U.S.C. §371 of PCT/KR2007/003514 filed on Jul. 20, 2007, which is incorporated herein by reference.

FIELD OF THE INVENTION

The present invention relates to a method for the preparation of dermal papilla tissue having hair follicle inducting ability.

BACKGROUND OF THE INVENTION

Hair follicles, among other cells, are formed and maintained through the interaction between epithelium and dermis, and it has been shown that dermal papilla plays a key role in the growth of the hair follicle (Cohen J., *J Embryol Exp Morphol.* 9:117-27, 1961; Oliver R F., *J Embryol Exp Morphol.* 15(3):331-47, 1966; and Oliver R F., *J Embryol Exp Morphol.* 18(1):43-51, 1967). In hair follicles, the dermal papilla interacts with the outer root sheath to induce hair formation and growth, and to maintain the hair cycle consisting of anagen, catagen and talogen. When alopecia caused by inheritance, male hormones or stress progresses, the dermal papilla undergoes gradual degradation, resulting in the degeneration of hair follicles.

There are various forms of hair loss, including male- or female-type alopecia and alopecia areata. In the past, alopecia was treated typically by various methods of implanting artificial hair into hair follicle root bulbs of the scalp, but such artificial hair implant methods had led to some serious problems, and such methods are now banned. Currently, there are two methods employed to treat alopecia: drug or natural substance therapy, and human hair transplantation. The drug or natural substance therapy may retard the progress of alopecia or prevent future hair loss, but it may accelerate hair loss when the medication is stopped after a prolonged use. On the other hand, the transplantation of human hair involves taking plugs of natural hair from occipital hair growing areas and transplanting them to bald areas. Although the transplanted hair settles at the transplant area as a complete hair follicle and becomes a permanent hair that undergoes a normal growth cycle, the number of hair to be transplanted is severely limited, and in case of transplanting about 2,000 hair strands per one operation, it is generally not possible to perform more than three such operations. Thus, the methods currently used for treating alopecia have a number of limitations, and to overcome such problems, many researchers have attempted to revive hair follicles by in vitro culturing hair follicle cells and implanting them in the treatment area.

When dermal papilla cells isolated from hair follicle are cultured, they show a structure similar to fibroblast cells of the skin. Such cultured papilla cells have the ability to induce hair follicle formation, which is supported by the fact that the cells tend to aggregate during culturing. In other words, the dermal papilla cells at the initial phase of cultivation aggregate with each other, unlike fibroblast cells of the skin. However, said ability is not sustained indefinitely and Reynolds et al. have reported that when dermal papilla cells are cultured in vitro, they gradually lose their innate hair follicle-inducting ability after about 3 to 4 passage numbers (Reynolds A J et al., *Development.* 122 (10):3085-94, 1996). On the other hand, Jahoda and Reynolds et al. have reported that when dermal papilla cells of rat's vibrissa hair cultured 3 passage numbers or less are implanted into small ear skin wounds and the back of rats, abnormally large hair fibers displaying vibrissa hair-type characteristics emerge from the transplant sites (Jahoda C A., *Development.* 115(4):1103-9, 1992; and Reynolds A J. et al., *Development.* 115(2):587-93, 1992). The above reports suggest that the primary cultivation period of dermal papilla cells in vitro should be short and efficient in order to obtain a large number of the cells for transplantation.

Generally, the yield of the primary cultivation decreases with the age of the tissues or organs from which the cultured cells are obtained. Accordingly, researchers have turned their attention from differentiated cells to embryonic stem cells or adult stem cells for cell therapy for the re-growth of hair. For example, Kataoka et al. have reported that when floated cells obtained from a mixture of mesenchymal stem cells originated from bone marrow of a mouse and epithelial/dermal cells of a fetus are transplanted, the regeneration of skin with hair growth occurred and that specific markers for the transplanted mesenchymal stem cells have been found in hair follicles. This observation suggests that the mesenchymal stem cells may also be effective for hair re-growth. Further, Richardson et al. have reported that hair follicle dermal cells can be differentiated into adipocyte and osteocyte, and Martin et al. have reported that both mesenchymal stem cells originated from bone marrow and hair follicle dermal stem cells differentiate into osteocyte, chondrocyte, adipocyte and myocyte.

The present inventors have paid attention to the fact that mesenchymal stem cells originating from bone marrow, adipose tissue or umbilical cord have characteristics similar to the cells constituting dermal papilla and dermal sheath, and accordingly, have attempted to develop an effective method for in vitro re-constitution of dermal papilla tissues.

SUMMARY OF THE INVENTION

Therefore, it is an object of the present invention to provide a method for the in vitro preparation of a dermal papilla tissue having hair follicle inducting ability.

In accordance with one aspect of the present invention, there is provided a method for the preparation of a large number of dermal papilla tissues which comprises the steps of:

1) culturing mesenchymal stem cells in a first culture medium which contains 600 to 1,900 mg/l of amino acids and 12 to 36 mg/l of vitamins;

2) culturing the cells obtained in step (1) in a second culture medium which contains 2,000 to 3,000 mg/l of amino acids and 40 to 60 mg/l of vitamins, wherein the medium is supplemented with a growth factor and free of serum;

3) adding trypsin or collagenase to the culture obtained in step (2) to allow a lump of cells to detach from the culture dish and undergo auto-aggregation to form a dermal papilla tissue; and 4) harvesting the dermal papilla tissue obtained in step (3) and culturing the tissue in the second culture medium.

BRIEF DESCRIPTION OF THE DRAWINGS

The above and other objects and features of the present invention will become apparent from the following description of the invention, when taken in conjunction with the accompanying drawings, which respectively show.

DETAILED DESCRIPTION OF THE INVENTION

The preparation method of the present invention characteristically comprises culturing mesenchymal stem cells originated from bone marrow, adipose tissue or umbilical cord in a conventional culture medium (primary culture medium) containing 600 to 1,900 mg/l of amino acids and 12 to 36 mg/l of vitamins (step 1), and culturing the primary cultured cells in a high concentration serum-free medium (secondary culture medium) containing 2,000 to 3,000 mg/l of amino acids and 40 to 60 mg/l of vitamins which is supplemented with 0.1 to 10,000 ng/ml of a growth factor (step 2) to prepare dermal papilla tissue.

In step (1) of the method of the present invention, mesenchymal stem cells originated from bone marrow, adipose tissue or umbilical cord are subjected to a primary culture in a common cell culture medium according to a conventional method in the art. The cell culture medium used for the primary culture in the present invention may be selected, but are not limited to, from the group consisting of DMEM (Dulbecco's Modified Eagle's Medium), DMEM/F-12, F-12, McCoy's 5A, RPMI1640, Williams' medium E and IMDM (Iscove's Modified Dulbecco's Medium). The mesenchymal stem cells can be proliferated through a series of primary culture steps up to 1 to 20 passage numbers.

In step (2) of the inventive method, the primary cultured cells are then cultured in the secondary culture medium which is a high concentration culture medium containing 2 to 5-fold higher concentrations of amino acids and vitamins than a common culture medium, together with a supplemented growth factor, without the use of any matrix or substrate. The growth factor employable in the present invention include, but are not limited to, HGF (hepatocyte growth factor), EGF (epidermal growth factor) and NGF (nerve growth factor), which may be added to the secondary culture medium in the amount ranging from 1 to 1000 ng/ml.

In step (3) of the inventive method, the culture obtained in step (2) is treated with trypsin or collagenase to detach the cells from the culture dish. The enzyme treatment gives the cells fluidity and induces auto-aggregation of the cells, reducing the time of formation of the aggregates, a dermal papilla tissue. When trypsin or collagenase is added to the culture medium, about 90% of the cells therein form auto-aggregates capable of reproducing the characteristics of dermal-forming cells within 72 hours. For example, in case of inoculating at $1 \times 10^6$ cells on 25 cm$^2$ culture dish, hundreds of auto-aggregates are formed.

In step (4) of the inventive method, the dermal papilla tissue formed in the previous step is isolated and preserved. For example, the culture medium containing the tissue (auto-aggregate) obtained in step (3) is subjected to centrifugation to harvest the auto-aggregated cells and the resulting precipitate is cultured in the culture medium used in step (2).

The dermal papilla tissue prepared by the inventive method can induce the formation of hair follicle through its interaction with a hair follicle lacking a dermal papilla, and form a new follicle having the hair cycle property or promote hair growth in existing hair follicles when transplanted into dermis of a nude mouse.

Since the secondary culture medium used in the present invention contains 2 to 5-fold higher amino acids and vitamins than the common culture medium mentioned above, it can overcome the problem of depleted nutrients and oxygen during the culture of mesenchymal stem cells, improving the differential characteristics of the cells, which results in helping the formation of the dermal papilla tissue.

Preferably, the secondary culture medium according to the present invention contains high concentrations of amino acids as follows: 30 to 200 mg/l each of L-arginine, L-asparagine, L-aspartatic acid, L-cystine.2HCl, L-isoleucine, L-leucine, and L-lysine.HCl; 30 to 210 mg/l each of L-phenylalanine, L-tryptophan, and L-tyrosine; and 50 to 600 mg/l each of the rest of the essential amino acids.

Further, it is preferable for the secondary culture medium of the present invention to contain high concentrations of vitamins as follows: 0.02 to 1 mg/l each of biotin, D-Ca pantothenate and riboflavin as a soluble vitamin B; 3 to 16 mg/l each of choline chloride, folic acid, niacinamide, pyridoxine.HCl, and thiamine.HCl; 10 to 15 mg/l of i-inositol; and 0.02 to 0.03 mg/l of vitamin $B_{12}$. More preferably, the medium of the present invention further comprises 0.03 to 0.07 mg/l of glutathione, 400 to 600 mg/l of glutamine, and 1,500 to 3,000 mg/l of D-glucose.

Further, more preferably, the secondary culture medium of the present invention comprises 3,000 to 3,500 mg/l of sodium bicarbonate (NaHCO$_3$) and 2,000 to 2,500 mg/l of HEPES (N-[2-hydroxyethyl] piperazine-N'-[2-ethanesulfonic acid]) having pH buffering effect; 1.0 to 2.0 mM of Ca and 0.5 to 1.0 mM of Mg that are trace elements essential for cell-cell adhesion; 0.25 to 0.7 nM each of Cu, Fe, Mn, and Zn, trace elements essential for cellular metabolism; and 4,000 to 5,000 mg/l of sodium chloride to adjust the osmotic pressure at 280 to 310 mOsm/kg.

Furthermore, for the purpose of prolonging the culture period of the hair follicle, the secondary culture medium of the present invention further comprises hydrocortisone (HC), insulin (I), transferrin (T), and sodium selenite (S). For example, it is preferable for the secondary culture medium to contain 10 to 100 μg/l of hydrocortisone, 5 to 20 mg/l of insulin, 5 to 20 mg/l of transferrin, and 0.005 to 0.02 mg/l of sodium selenite.

It is still more preferable to use a secondary culture medium comprising 165 mg/l of CaCl$_2$, 0.0001 mg/l of CuSO$_4$.5H$_2$O, 0.0001 mg/l of Fe(NO$_3$).9H$_2$O, 330 mg/l of KCl, 0.076 mg/l of KNO$_3$, 98 mg/l of MgSO$_4$, 0.0001 mg/l of MnCl$_2$.4H$_2$O, 4,800 mg/l of NaCl, 3,360 mg/l of NaHCO$_3$, 111 mg/l of Na$_2$HPO$_4$, 0.0002 mg/l of ZnSO$_4$.7H$_2$O, 2,000 mg/l of D-glucose, 110 mg/l of sodium pyruvate, 2,383 mg/l of HEPES, 15 mg/l of phenol red, 50 mg/l of L-alanine, 100 mg/l of L-arginine, 50 mg/l of L-asparagine, 60 mg/l of L-aspartic acid, 182.4 mg/l of L-cystine.2HCl, 150 mg/l of L-glutamic acid, 584 mg/l of L-glutamine, 60 mg/l of L-glycine, 62.1 mg/l of L-histidine, 210 mg/l of L-isoleucine, 210 mg/l of L-leucine, 292 mg/l of L-lysine.HCl, 60 mg/l of L-methionine, 132 mg/l of L-phenylalanine, 80 mg/l of L-proline, 84 mg/l of L-serine, 190 mg/l of L-threonine, 32 mg/l of L-tryptophan, 208 mg/l of L-tyrosine, 188 mg/l of L-valine, 0.026 mg/l of biotin, 0.026 mg/l of D-Ca pantothenate, 8 mg/l of choline chloride, 16 mg/l of folic acid, 14.40 mg/l of i-inositol, 8 mg/l of niacinamide, 8 mg/l of pyridoxine.HCl, 0.8 mg/l of riboflavin, 3 mg/l of thiamine.HCl, and 0.026 mg/l of vitamin $B_{12}$.

The secondary culture medium preferably used in the present invention comprises 2-fold higher concentrations of amino acids and vitamins than a common culture medium used in the art to provide energy for cellular metabolism and maintain cell activity. The level therein of D-glucose, which is metabolized into lactic acid and plays a less important role as an energy source, is lower. The concentration of L-glutamine in the secondary culture medium which affects on the amount of ATP synthesis is fixed to 4 mM. Further, the secondary culture medium comprises 0.7 nM of zinc, 0.25 nM of iron, 0.4 nM of copper, and 0.5 nM of manganese as trace elements, and contains sodium bicarbonate and HEPES having pH buffering capability at concentrations of 40 mM and 10 mM, respectively. The secondary culture medium of the present invention comprises calcium and magnesium as essential minerals for intercellular adhesion at final concentrations of 1.5 mM and 0.8 mM, respectively, and also contains 4,500 mg/l of sodium chloride to adjust the osmotic pressure to the range of 280 to 310 mOsm/kg.

In addition, the secondary culture medium of the present invention may further comprise 10 mg/l of transferrin as an iron source; 0.01 mg/l of sodium selenite as an inorganic salt; 10 μg/t of hydrocortisone, 10 mg/l of insulin and 0.2 weight % of albumin as a hormone; and 20 ng/ml of a growth factor.

Further, the secondary culture medium of the present invention is preferably maintained at a constant pH, which is an important factor for cell culture, through the buffering interaction between the bicarbonate salt and the metabolite. Namely, since the secondary culture medium of the present invention has higher concentrations of amino acids than a common culture medium such as Williams' medium E, there is the possibility of increasing pH as the concentration of ammonia, the final metabolite of amino acids, increases. But, the added bicarbonate salt as a buffering agent maintains the medium's pH 7.2 to 7.5.

Copper sulfate in the secondary culture medium of the present invention suppresses apoptosis caused by radical ions through the action of superoxide dismutase (SOD) which is a copper dependent enzyme and antioxidant present in the hair follicle, and stimulates the synthesis of a natural growth factor and extracellular matrix by inhibiting both 5α-reductase-1 and -2 through the action of other copper dependent enzymes. Further, zinc is an essential mineral component for the activation of a zinc finger transcription factor.

The dermal papilla tissue prepared according to the present invention is an aggregate consisting of dermal papilla cells differentiated from mesenchymal stem cells and has a size about 100-200 μm similar to that of the intact dermal papilla, and shows a strong direct cell-cell interaction because it is prepared by through natural cellular contact. Histological observations of a section of the aggregate with hematoxylin/eosin indicate that the cells are tightly aggregated. Further, the dermal papilla tissue prepared according to the present invention exhibits the expression of type 4 collagen and laminin, components of basilar membrane of intact dermal papilla, and also the expression of versican, a marker for identifying hair follicle inductive potency. Since the aggregate does not require any external stimulation or a matrix for cell adhesion and proliferation, it can be mass produced. Such aggregates show high hair follicle inducting ability, which can be effectively used for the treatment of alopecia through cell transplantation and for in vitro studies for the hair follicle characteristics.

The following Examples are intended to further illustrate the present invention without limiting its scope.

Preparation Example 1

Preparation of a Secondary Culture Medium

One liter of a medium containing higher concentration, of amino acids and vitamins than conventional culture media was prepared according to the composition described in Tables 1a to 1d, and 10 mg/l of insulin, 10 mg/l of transferrin, 0.01 mg/l of sodium selenite, 10 μg/l of hydrocortisone, and 0.2 weight % of albumin (2 g/l) were added thereto, to prepare a secondary culture medium.

TABLE 1a

| Inorganic salts (mg/l) | |
|---|---|
| $CaCl_2$ | 165 |
| $CuSO_4 \cdot 5H_2O$ | 0.0001 |
| $Fe(NO_3) \cdot 9H_2O$ | 0.0001 |
| KCl | 330 |
| $KNO_3$ | 0.076 |
| $MgSO_4$ | 98 |
| $MnCl_2 \cdot 4H_2O$ | 0.0001 |
| NaCl | 4800 |
| $NaHCO_3$ | 3360 |
| $Na_2HPO_4$ | 111 |
| $ZnSO_4 \cdot 7H_2O$ | 0.0002 |

TABLE 1b

| Other ingredients (mg/l) | |
|---|---|
| D-glucose | 2000 |
| Sodium pyruvate | 110 |
| HEPES | 2383 |
| Phenol red | 15 |

TABLE 1c

| Amino acids (mg/l) | |
|---|---|
| L-alanine | 50 |
| L-arginine | 100 |
| L-asparagine | 50 |
| L-aspartic acid | 60 |
| L-cystine•2HCl | 182.4 |
| L-glutamic acid | 150 |
| L-glutamine | 584 |
| L-glycine | 60 |
| L-histidine | 62.1 |
| L-isoleucine | 210 |
| L-leucine | 210 |
| L-lycine•HCl | 292 |
| L-methionine | 60 |
| L-phenylalanine | 132 |
| L-proline | 80 |
| L-serine | 84 |
| L-threonine | 190 |
| L-tryptophan | 32 |

TABLE 1c-continued

| Amino acids (mg/l) | |
|---|---|
| L-tyrosine | 208 |
| L-valine | 188 |

TABLE 1e

| Vitamins (mg/l) | |
|---|---|
| Biotin | 0.026 |
| D-Ca pantothenate | 0.026 |
| Choline chloride | 8 |
| Folic acid | 16 |
| i-inositol | 14.40 |
| Niacinamide | 8 |
| Pyridoxine•HCl | 8 |
| Riboflavin | 0.8 |
| Thiamine•HCl | 3 |
| Vitamin $B_{12}$ | 0.026 |

Example 1

Obtainment of Mesenchymal Stem Cells

Figure 1A:
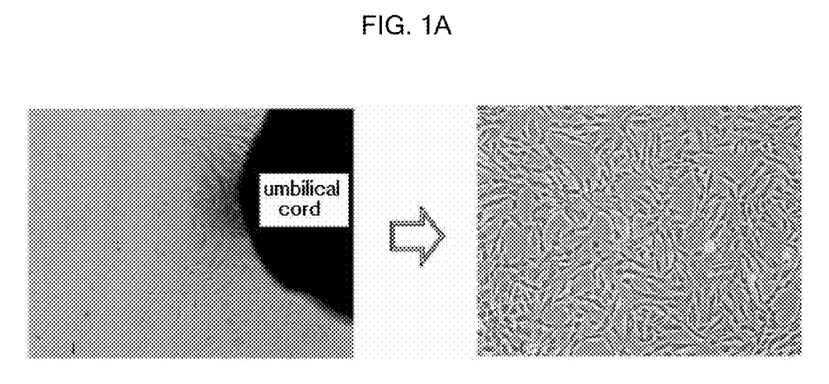
FIG. 1A: an optical microscope picture showing the effluxion of the mesenchymal stem cells from the Wharton jelly layer of the umbilical cord and the structure of the cells.
Figure 1B:
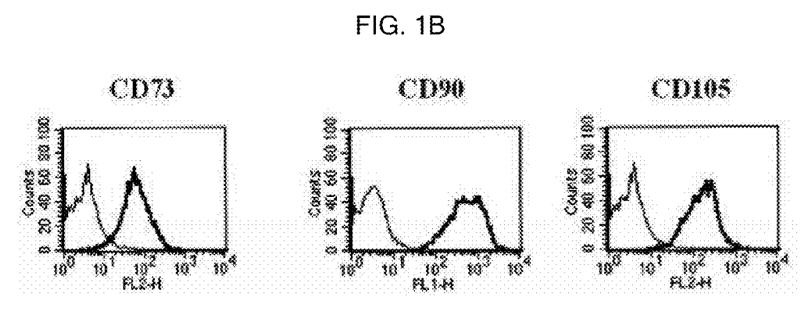
FIG. 1B: the result of flow cytometry for mesenchymal stem cells originated from bone marrow and umbilical cord.

Umbilical cord obtained during parturition was washed 3 times with phosphate buffer, and the smooth muscle area around blood vessels and the epithelial layer were removed therefrom. The remaining Wharton jelly layer was cut into small pieces of about 3 mm×3 mm in size and the pieces were placed on a culture dish, and in an incubator maintained at 37° C. for about 4 hours until the pieces adhered to the bottom of the culture dish. Then, DMEM (Dulbecco's Modification of Eagle's Medium) supplemented with 10% FBS was added to the culture medium. 1 week thereafter, cells began to flow out from the Wharton jelly of the umbilical cord, and when the cells occupied about 80% of the bottom of culture dish, the medium was shifted to a new medium in which the cells were sub-cultured. When the cells grew to occupy about 70% of the culture dish, the medium was treated with 0.05% trypsin/0.02 EDTA to detach the cells from the culture dish and adjusted the concentration to $5 \times 10^5$ cells/ml. Then, the cells were allowed to react with the antibodies of CD73, CD90 and CD105, the markers of stem cells, for 20 minutes. The cell solution was washed with two fold volume of PBS and fixed with a flow buffer solution (1% paraformaldehyde, 0.1% sodium azide and 0.5% BSA in PBS). Then, the cell solution was subjected to flow cytometry using FACScan (BD science) and analyzed with CELLQUEST software (BD science). The result showed that the cells contained CD73, CD90 and CD105 (FIG. 1B).

Figure 1C:
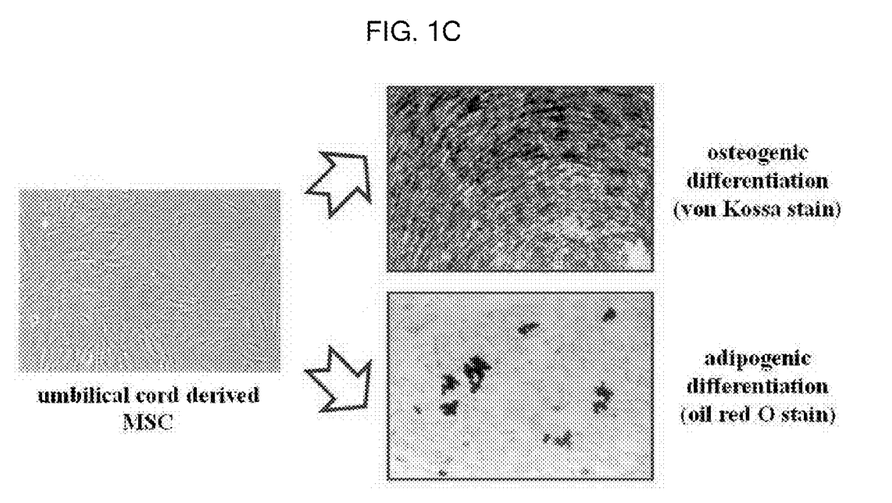
FIG. 1C: photographs showing the osteogenic and adipogenic differentiation of mesenchymal stem cells originated from umbilical cord.

Further, in order to check the differentiating ability of the cells, they were inoculated into a 6-well plate and DMEM containing low concentration glucose and supplemented with 10% serum was added thereto. The cells were cultured until they occupied about 70% of the culture dish. Then, the culture medium was replaced with new mediums for osteogenic or adipogenic differentiation. The medium for osteogenic differentiation was DMEM supplemented with 100 nM of dexamethasone, 0.05 mM of ascorbic acid 2-phosphate, 10 mM of β-glycerophosphate, $10^{-8}$ M of vitamin $D_3$ and 10% FBS, and the medium was replaced with a fresh medium at about 3-day intervals. 3 weeks thereafter, the cells were identified as stem cells by the Von Cossa staining method (FIG. 1C). Further, as the medium for adipogenic differentiation, DMEM supplemented with 1 μM of dexamethasone, 0.05 mM of methyl-isobutylxanthaine (IBMX), 10 μg/ml of insulin, 100 mM idomethacin and 10% FBS was employed. 3 days after culturing the cells in the medium, it was replaced with DMEM supplemented with 10 μg/ml of insulin and 10% FBS and the cells were cultured in the replaced medium for 1 day. The medium was replaced with a fresh medium at about 3-day intervals. 3 weeks thereafter, the cells were identified as stem cells by oil red O staining (FIG. 1C).

The mesenchymal stem cells originated from bone marrow and adipose tissue were purchased from Cell Applications Inc. (USA) and were identified as stem cells by the methods disclosed in the articles (Schilling et al., *Mol and Cell Endocrinol.*, 271(1-2), 1-17, 2007; Kern et al., *Stem Cells*, 24(5), 1294-1301, 2006).

Example 2

Preparation of a Dermal Papilla Tissue

Mesenchymal stem cells originated from bone marrow, adipose tissue and umbilical cord obtained in Example 1 were respectively subjected to a monolayer culture in DMEM supplemented with 10% FBS until the cells occupied about 80% of the culture dish. Then, the culture medium was replaced with a secondary culture medium which is a serum-free high concentration medium prepared in Preparation Example 1, and 20 ng/ml of HGF (rhHGF, R&D system) was added thereto. The medium was replaced with a fresh medium at about 3-day intervals, and 3 weeks thereafter, the culture was treated with trypsin in an amount ranging from 20 to 40 μl/cm² to detach the cells from the culture dish. Cell aggregation began to take place from about 24 hours after treating with trypsin, and the completely aggregated cell mass became suspended in the medium. The suspended cell aggregates were isolated from the culture using centrifugation at 500 rpm for 3 min. The cell aggregates were re-suspended in a fresh medium and kept at a culture container to preserve their culturing state until they are used in the following experiment.

Figure 2:
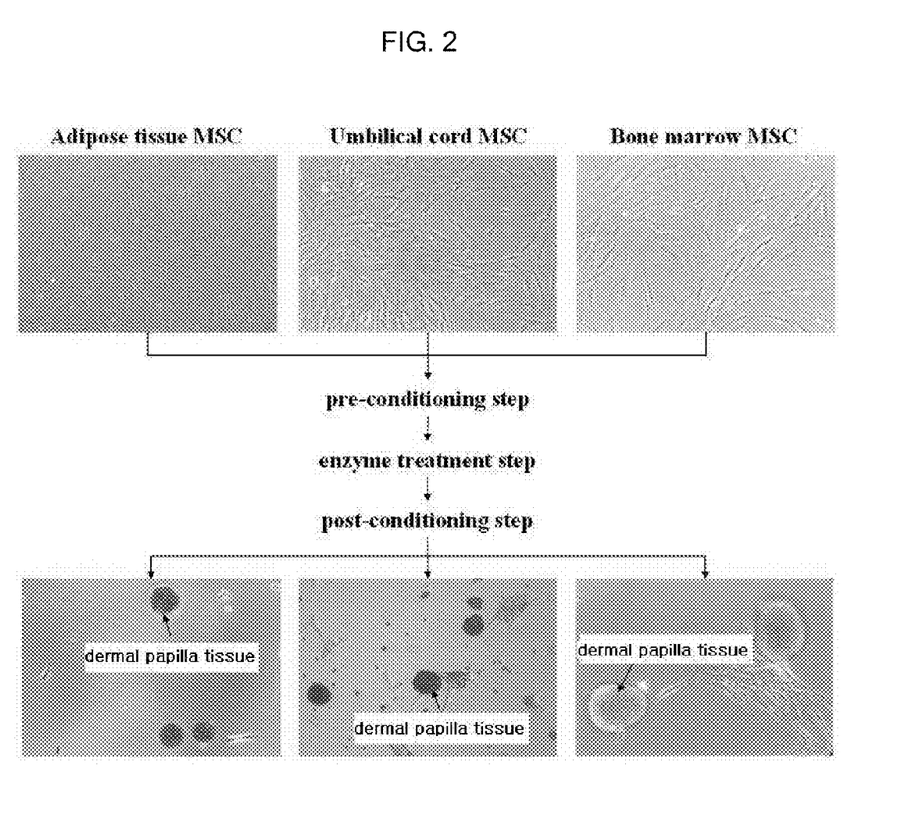
FIG. 2: photographs showing the process of the formation of dermal papilla tissues from mesenchymal stem cells originated from bone marrow, adipose tissue and umbilical cord in vitro, and the structure of the dermal papilla tissue.

FIG. 2 illustrates the process for the formation of a dermal papilla tissue from a mesenchymal stem cell originated from bone marrow, adipose tissue and umbilical cord in vitro, and the structure of the mesenchymal stem cell.

Test Example 1

Identification of a Dermal Papilla Tissue

The size and the contact section of the dermal papilla tissue prepared according to the method described in Example 2 were observed with a hematoxylin/eosin histological staining method. The result shown in FIG. 3 reveals that the cells are tightly aggregated, and resistant to disintegration by an external stimulation. Further, size of the aggregates is about 100-200 μm, similar to natural dermal papilla tissue.

Figure 3:
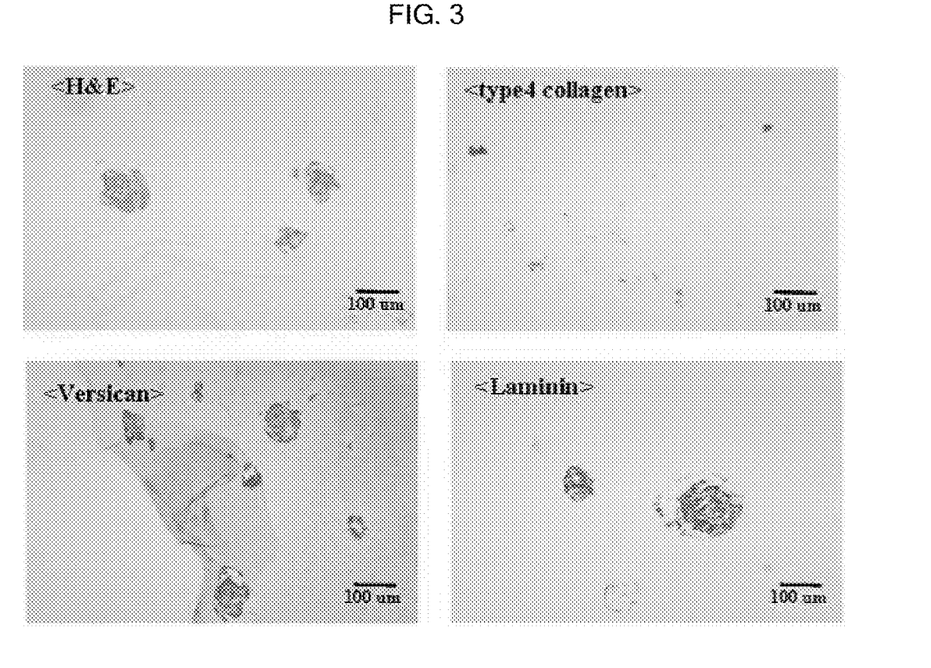
FIG. 3: photographs showing that the dermal papilla tissue of the present invention has constituents similar to those of dermal papilla of intact hair follicle and has hair follicle inductive ability.

Further, in order to confirm whether type 4 collagen and laminin, components of the basilar membrane of natural dermal papilla, and versican, a marker for verifying hair follicle inductive potency, were expressed in the dermal papilla tissue prepared in Example 2, the methods disclosed in the articles (Katsuoka et al., *Arch Dermtol Res*, 280(3), 140-144. 1988; Bratka-Robia et al., *Vet Dermatol*, 12(1), 1-6, 2002; Soma et al., *J Dermatol Sci.*, 39(3), 147-154, 2005) were employed. The result showed that they were all expressed in the inventive dermal papilla tissue (FIG. 3).

Test Example 2

Formation of Hair Follicles by Using an Artificial Dermal Papilla Tissue

In order to examine whether the dermal papilla tissue prepared in Example 2 can induce the formation of the hair follicle, an experiment was conducted as follows.

Figure 4:
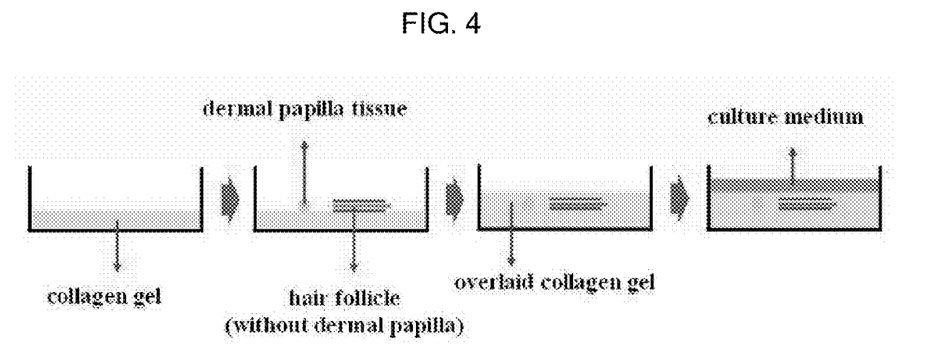
FIG. 4: a diagram of the experiment used for observing the interaction between dermal papilla tissues and a hair follicle lacking a dermal papilla in Test Example 2.

Each well of a 24-well plate was filled with about 700 μl of a collagen solution and kept in a 37° C. incubator for 1 hr to induce gelation. The dermal papilla tissue prepared in Example 2 and hair follicle lacking dermal papilla was placed on the collagen gel such that there formed a gap of 300 μm between them, followed by culturing for 5 to 10 min to allow them to attach to the gel surface. After 700 μl of the collagen solution was poured thereon and subjected to gelation, a K-SFM culture medium (Gibco BRL, N.Y., U.S.A.) was added thereto. A diagram of this experiment is shown in FIG. 4.

Figure 5:
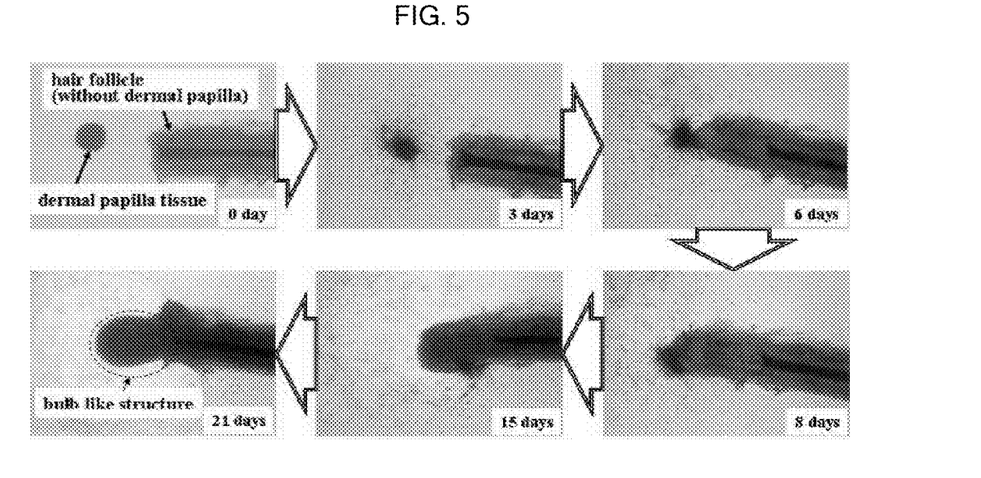
FIG. 5: photographs showing the formation of a hair bulb in vitro when a dermal papilla tissue prepared by the inventive method is co-cultured with a hair follicle lacking a dermal papilla.

After about 1 week, outer root sheath cells were induced to surround the dermal papilla. It was observed that the number of the outer root sheath cells was high enough to form a hair bulb structure after about 15 days and a new hair bulb was formed after about 21 days (FIG. 5).

These appearances are substantially identical as previous reported in an article (Arase et al., Skin Pharmacol, 7(1-2), 12-15, 1994) which disclosed the formation of a new bulblike structure by co-culturing a dermal papilla of human hair follicle and a hair follicle lacking the dermal papilla. Accordingly, it has been verified that the dermal papilla tissue prepared according to the present invention has the same hair follicle inductive ability as a natural dermal papilla tissue.

Test Example 3

Induction of Formation of Hair Follicle In Vivo by Using an Artificial Dermal Papilla Tissue About 100 to 150 pieces of the dermal papilla tissue prepared in Example 2 and outer root sheath cells ($3\times10^6$ cells) were dispersed together in 100 μl of physiological saline, and 50 μl of the resulting mixture was injected into the intradermis of dorsal skin of nude mice using 1 ml syringe, followed by putting a mark on the injection point.

Figure 6:
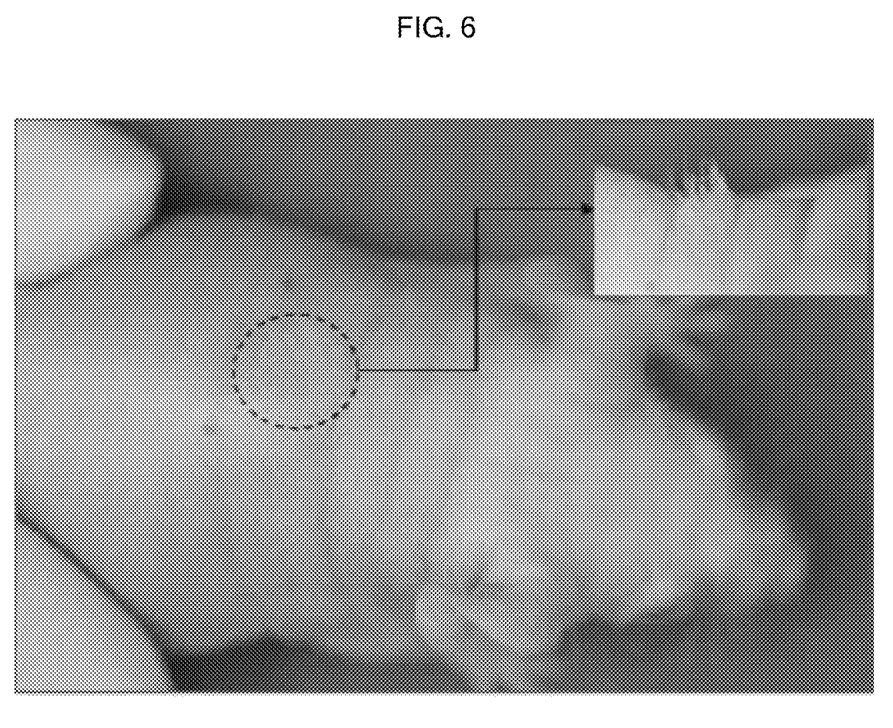
FIG. 6: photographs showing the hair growth, after dermal papilla tissues prepared by the inventive method and outer root sheath cells are injected into the intra-dermis of dorsal skin of a nude mouse.

As a result, hair growth was observed on the marked area 45 days after injection, implying that the dermal papilla tissue prepared according to the present invention has hair follicle inducting ability in vivo (FIG. 6).

While the invention has been described with respect to the above specific embodiments, it should be recognized that various modifications and changes may be made to the invention by those skilled in the art which also fall within the scope of the invention as defined by the appended claims.

What is claimed is:

1. A method for the preparation of a dermal papilla tissue, which comprises the steps of:
   1) culturing mesenchymal stem cells in a first culture medium, said first culture medium being an animal cell culture medium and containing 600 to 1,900 mg/l of amino acids and 12 to 36 mg/l of vitamins;
   2) culturing the cells obtained in step (1) in a second culture medium which contains 2,000 to 3,000 mg/l of amino acids and 40 to 60 mg/l of vitamins, wherein the second culture medium is supplemented with one or more growth factors selected from the group consisting of hepatocyte growth factor, epidermal growth factor and nerve growth factor, and wherein the second culture medium is free of serum;
   3) adding trypsin or collagenase to the culture obtained in step (2) to allow a lump of cells to detach from the culture dish and undergo auto-aggregation to form a dermal papilla tissue; and
   4) harvesting the dermal papilla tissue obtained in step (3) and culturing the tissue in the second culture medium.

2. The method of claim 1, wherein the mesenchymal stem cells are originated from bone marrow, adipose tissue or umbilical cord.

3. The method of claim 1, wherein the first culture medium is selected from the group consisting of Dulbecco's Modified Eagle Medium (DMEM), DMEM/F-12, F-12, McCoy's 5A, RPMI 1640, Williams' medium E, and Iscove's Modified Dulbecco's Medium).

4. The method of claim 1, wherein the mesenchymal stem cells are cultured in step (1) up to 1 to 20 passage numbers.

5. The method of claim 1, wherein the growth factors are employed in an amount ranging from 1 to 1000 ng/ml.

6. The method of claim 1, wherein the second culture medium comprises 30 to 200 mg/l each of L-arginine, L-asparagine, L-aspartatic acid, L-cystine.2HCl, L-isoleucine, L-leucine, and L-lysine.HCl; 30 to 210 mg/l each of L-phenylalanine, L-tryptophan, and L-tyrosine; 50 to 600 mg/l each of L-alanine, L-glutamic acid, L-glycine, L-histidine, L-methionine, L-proline, L-serine, L-threonine, and L-valine; 0.01 to 2 mg/l each of biotin, D-Ca pantothenate and riboflavin; 3 to 16 mg/l each of choline chloride, folic acid, niacinamide, pyridoxine.HCl, and thiamine.HCl; 10 to 15 mg/l of i-inositol; 0.02 to 0.03 mg/l vitamin $B_{12}$; 400 to 600 mg/l of glutamine; 1,500 to 3,000 mg/l of D-glucose; 3,000 to 3,500 mg/l of sodium bicarbonate ($NaHCO_3$); 2,000 to 2,500 mg/l of HEPES (N-[2-hydroxyethyl] piperazine-N'-[2-ethanesulfonic acid]); 1.0 to 2.0 mM of Ca; 0.5 to 1.0 mM of Mg; 0.25 to 0.7 nM each of Cu, Fe, Mn, and Zn; and 4,000 to 5,000 mg/l of sodium chloride.

7. The method of claim 1, wherein the second culture medium further comprises insulin, transferrin, sodium selenite, hydrocortisone and albumin.

8. The method of claim 1, wherein the dermal papilla tissue is an aggregate consisting of the cells differentiated from the mesenchymal stem cells.

* * * * *